(12) United States Patent
Bevacqua et al.

(10) Patent No.: US 10,004,671 B2
(45) Date of Patent: Jun. 26, 2018

(54) TOPICAL EMULSIONS COMPRISING INDIUM TIN OXIDE COATED PARTICLES

(71) Applicant: ELC Management LLC, Melville, NY (US)

(72) Inventors: Andrew Bevacqua, Jericho, NY (US); Craig Bonda, Winfield, IL (US); Linda Najdek, East Islip, NY (US); Fatemeh Mohammadi, Hauppauge, NY (US); Milan Franz Sojka, Coram, NY (US); Vasile Ionita-Manzatu, Bethpage, NY (US); Thomas Mammone, Farmingdale, NY (US)

(73) Assignee: ELC Management LLC, Melville, NY (US)

( * ) Notice: Subject to any disclaimer, the term of this patent is extended or adjusted under 35 U.S.C. 154(b) by 0 days. days.

(21) Appl. No.: 15/339,319

(22) Filed: Oct. 31, 2016

(65) Prior Publication Data

US 2017/0340530 A1 Nov. 30, 2017

Related U.S. Application Data

(60) Provisional application No. 62/354,207, filed on Jun. 24, 2016, provisional application No. 62/253,269, filed on Nov. 10, 2015.

(51) Int. Cl.
| | | |
|---|---|---|
| *A61Q 17/04* | (2006.01) | |
| *A61K 8/22* | (2006.01) | |
| *A61K 8/02* | (2006.01) | |

(52) U.S. Cl.
CPC .............. *A61K 8/22* (2013.01); *A61K 8/0245* (2013.01); *A61Q 17/04* (2013.01)

(58) Field of Classification Search
CPC ..................................................... A61Q 17/04
See application file for complete search history.

(56) References Cited

U.S. PATENT DOCUMENTS

| | | |
|---|---|---|
| 3,215,724 A | 11/1965 | Strobel et al. |
| 3,781,417 A | 12/1973 | Welters et al. |
| 4,373,013 A | 2/1983 | Yoshizumi |
| 4,828,825 A * | 5/1989 | Weber ............... A61K 8/19 424/59 |
| 6,143,405 A | 11/2000 | Falmgren |
| 6,613,383 B1 | 9/2003 | George et al. |
| 6,713,177 B2 | 3/2004 | George et al. |
| 6,913,827 B2 | 7/2005 | George et al. |
| 7,132,697 B2 | 11/2006 | Weimer et al. |
| 7,396,862 B2 | 7/2008 | Weimer et al. |
| 8,133,531 B2 | 3/2012 | King et al. |
| 8,163,336 B2 | 4/2012 | Weimer et al. |
| 8,187,731 B2 | 5/2012 | Weimer et al. |
| 8,637,156 B2 | 1/2014 | Weimer et al. |
| 8,992,897 B2 | 3/2015 | Niki et al. |
| 9,139,737 B1 | 9/2015 | Shah et al. |
| 9,196,901 B2 | 11/2015 | Se-Hee et al. |
| 2003/0124167 A1 | 7/2003 | Thies |
| 2006/0154071 A1 | 7/2006 | Homma et al. |
| 2008/0173845 A1 | 7/2008 | Ryowa et al. |
| 2009/0233090 A1 | 9/2009 | Wong et al. |
| 2010/0202985 A1 | 8/2010 | SenGupta |
| 2011/0091510 A1 | 4/2011 | Lele et al. |
| 2011/0233490 A1 | 9/2011 | Tsai et al. |
| 2011/0272668 A1 | 11/2011 | Taylor et al. |
| 2011/0284364 A1 | 11/2011 | Margadant et al. |
| 2012/0015015 A1 | 1/2012 | Kim et al. |
| 2014/0030339 A1 | 1/2014 | Leblanc et al. |
| 2014/0154191 A1 | 6/2014 | Doucet et al. |

FOREIGN PATENT DOCUMENTS

| | | |
|---|---|---|
| JP | 61-18708 | 1/1986 |
| WO | WO-2017/083117 | 5/2017 |

OTHER PUBLICATIONS

Buonsanti, et al.; "Tunable Infrared Absorption and Visible Transparency of Colloidal Aluminum-Doped Zinc Oxide Nanocrystals" Nano Letters pubs.acs.org/NanoLett, pp. A-E; ACS Publications; Jul. 12, 2011.

Butcher et al., Detailed analysis of absorption data for indium nitride, Materials Science in Semiconductor Processing 6, 2003, 351-354, Elsevier Ltd., Australia.

Cho et al., Effects of Infrared Radiation and Heat on Human Skin Aging in vivo, Journal of Investigative Dermatology Symposium Proceedings, 2009, 15-19, 14, Seoul, Korea.

Devika, Mudusu et al., "ZnO/ITO core/shell nanostructure electrodes for future prototype solar cell devices,"; RSC Advances, Dec. 3, 2014 (e-pub), vol. 5, No. 4, pp. 2891-2899 See p. 2892, left column, line 15-right column, line 27; and figures 2-6.

Holzer, et al.; The Other End of the Rainbow: Infrared and Skin; J. Invest Dermatol; Jun. 2010; 130(6); 1496-1499; pp. 1-5.

J.-J. Nam et al., Metal oxide-coating PMMA or Talc as a new IR blacker inhibits IR-induced decrease of collagens in human dermal fibroblasts, International Journal of Cosmetic Science, 2015, 433-437, 37.

Jiang, Chao et al., "Fabricating transparent multilayers with UV and near-IR double-blocking properties through layer-by-layer assembly," Industrial & Engineering Chemistry Research, 2013, vol. 52, No. 37, pp. 13393-13400; See abstract; p. 13394, left column, line 24-right column, line 31; and scheme 1.

Lee, Ju Hee, et al.; Effects of Infrared Radiation on Skin Photo-Aging and Pigmentation; Yonsei Medical Journal; vol. 47, No. 4; pp. 485-490; 2006.

Martin Fritz and Friedrich Waibel; Coating Materials; Springer Series in Optical Sciences, 2003; pp. 105-130.

PCT International application No. PCT/US2016/059404; Applicant: ELC Management LLC; International filing date: Oct. 28, 2016; Priority date: Nov. 10, 2015.

(Continued)

*Primary Examiner* — Carlos A Azpuru

(74) *Attorney, Agent, or Firm* — Julie M. Blackburn

(57) ABSTRACT

A solid or hollow particle ranging from 0.001 to 200 microns in diameter coated with Indium Tin Oxide ("ITO") and a topical composition containing same as well as a method for protecting skin against IR radiation.

9 Claims, No Drawings

(56) References Cited

OTHER PUBLICATIONS

PCT International Search Report; International Application No. PCT/US2016/059404; dated Feb. 10, 2017; Completion Date: Feb. 10, 2017.
PCT International Search Report; International Application No. PCT/US2016/059421; Completion Date: Feb. 10, 2017; dated Feb. 10, 2017.
PCT International Search Report; International Application No. PCT/US2016/060507; dated Mar. 6, 2017; Completion Date: Mar. 6, 2017.
PCT Written Opinion of the International Searching Authority; International Application No. PCT/US2016/060507; Completion Date: Mar. 6, 2017; dated Mar. 6, 2017.
PCT Written Opinion of the International Searching Authority; International Application No. PCT/US2016/059404; Completion Date: Feb. 10, 2017; dated Feb. 10, 2017.
PCT Written Opinion of the International Searching Authority; International Application No. PCT/US2016/059421; Completion Date: Feb. 10, 2017; dated Feb. 10, 2017.
Psuja, P. et al., "Fabrication and luminescent properties of ITO nanocrystalline coated micro Eu:Y2O3 particles,"; Proceedings of SPIE, 2008, vol. 6988, article No. 69881S, internal pp. 1-8 See abstract; p. 2, lines 17-29; p. 3, line 10; and figures 2, 3.
Wang, Jeng-Han; Low-pressure organometallic chemical vapor deposition of indium nitride on titanium dioxide nanoparticles; Chemphyschem; Oct. 2004, 5, 1615-1618; Wiley-VCH Verlag GmbH & Co. KGaA, Weinheim.
Zhang, J., et al.; Sol-gel preparation of poly (ethylene glycol) doped indium tin oxide thin films for sensing applications; Optical Materials; vol. 26, Issue 1; Jun. 2004; pp. 1-6.
Aton M. Holzer, MD; The Other End of the Rainbow: Infrared and Skin; J Invest Dermatol. Jun. 2010; 130(6): 1496-1499. doi:10.1038/jid.2010.79; National Institute of Health; NIH Public Access.
David Valdesueiroas; Gas-Phase Deposition of Ultrathin Aluminium Oxide Films on Nanoparticles at Ambient Conditions; Materials 2015, 8, 1249-1263; doi:10.3390/ma8031249; Open Access materials ISSN 1996-1944; www.mdpi.com/journal/materials.
Harry Zervos; The market for touch screens and ITO replacement; 2012 IDTechEx; www.IDTechEx.com.
http://www.gnpd.com; Mintel; Comfort Cream SPF 50; Record ID: 2001201; Company: Coty; Brand: Lancaster Sun for Kids Wet Skin; Category: Skincare; Sub-Category:Sun—Sun/Sunbed; Exposure; Country: UK.
Indium Tin Oxide (ITO) for deposition of transparent conductive oxide layers; High Density Ceramic TCO Sputtering Targets; Umicore Thin Film Products;BV868857/3/2013/1000.
Jeffrey W. Elam; Atomic Layer Deposition of Indium Tin Oxide Thin Films Using Nonhalogenated Precursors; J. Phys. Chem. C 2008, 112, 1938-1945; ReceiVed: Oct. 4, 2007; In Final Form: Nov. 8, 2007.
Jeng-Han Wang; Low-pressure organometallic chemical vapor deposition of indium nitride on titanium dioxide nanoparticles; ChemPhysChem 2004, 5, 1615-1618; 2004 Wiley-VCH Verlag GmbH & Co. KGaA, Weinheim; www.chemphyschem.org.
Jones, Charles E.; Use of SunSpheres technology to increase the effective SPF and UVA absorbance of personal care products containing UV actives; New Developments in UV Sunscreens; Rohm and Haas Company; PCIA 2005; Bangkok, Thailand.
Ju Hee Lee; Effects of Infrared Radiation on Skin Photo-Aging and Pigmentation; Yonsei Medical Journal vol. 47, No. 4, pp. 485-490, 2006.
Liu Wei; Photoelectric properties of ITO thin films deposited by DC magnetron sputtering; vol. 32, No. 1; Journal of Semiconductors; Jan. 2011; pp. 013002-1 through 013002-4; DOI: 10.1088/1674-4926/32/1/013002; PACC: 7360F; 7870C; 8115G; 2011 Chinese Institute of Electronics.
Ming-Jong, Keum, et al.; Preparation of ITO Thin Film by Using DC Magnetron Sputtering; Journal of the Korean Physical Society; vol. 53, No. 3, Sep. 2008; pp. 1580-1583.
Soyun Cho; Effects of Infrared Radiation and Heat on Human Skin Aging in vivo; Journal of Investigative Dermatology Symposium Proceedings (2009), vol. 14 2009 ;The Society for Investigative Dermatology; www.jidonline.org.
Steven M. George; Atomic Layer Deposition: An Overview; Chem. Rev. 2010, 110, 111-13; 2010 American Chemical Society Published on Web Nov. 30, 2009.
Tadatsugu Minami; Optical Properties of Aluminum Doped Zinc Oxide Thin Films Prepared by RF Magnetron Sputtering; ; Japanese Journal of Applied Physics; vol. 24, No. 8; Aug. 1985,; . pp. L605-L607; Received May 27, 1985; accepted for publication Jul. 20, 1985.
15th edition of Remington's Pharmaceutical Sciences on p. 1154, 1975.
Samoilov, V.M.; Specific Surface Area, Shape, and Size of Fine Carbon Filler Particles; Inorganic Materials; vol. 46; No. 8; pp. 818-823; 2010.

\* cited by examiner

TOPICAL EMULSIONS COMPRISING INDIUM TIN OXIDE COATED PARTICLES

TECHNICAL FIELD

The invention is in the field of compositions for topical application to keratin surfaces containing Indium Tin Oxide coated particles.

BACKGROUND OF THE INVENTION

The undesirable effects of ultraviolet radiation on skin are well known. Ultraviolet light is electromagnetic radiation with wavelengths ranging from 100 to 400 nm. UV wavelengths are shorter than those of visible light (which ranges from 400 to 700 nm) but longer than the wavelengths found in X-rays. UV light can be further categorized into UVA, UVB, and UVC. UVA light has wavelengths ranging from 315 to 400 nm. UVB light has wavelengths ranging from 280 to 315 nm. UVC has wavelengths ranging from 100 to 280 nm. UV light can also be categorized by near UV ("NUV") which is 300 to 400 nm, middle UV ("MUV") which is 200 to 300, and far UV ("FUV") which is 122 to 200 nm. It has been shown that exposure to UV light can result in immediate skin tanning or burning and, over time and repeated exposure, increase skin photo aging, which manifests in conditions such as wrinkles, lines, skin laxity and uneven pigmentation.

However, less well documented are the effects of infrared ("IR") light on skin. IR light spans wavelengths ranging from 760 nm to 1 mm and is subdivided into three regions of increasing wavelength: IR-A from 760 nm to 1400 nm, IR-B from 1400 to 3000 nm, and IR-C from 3000 nm to 1 mm. The solar energy that reaches the earth's surface spans the UV, visible, and IR wavelength ranges. Nearly one half of that solar energy is in the IR range and transmitted in the form of heat. It is known that chronic heat exposure can cause certain skin conditions similar to what is seen in photo-aged skin. For example, a condition known as erythema ab igne results in symptoms such as hyperpigmentation, reticulated erythema, scaling, and telangiectasis in skin surfaces that are exposed to IR radiation over longer periods of time. People who spend a lot of time in heat conditions, such as bakers or jewelers, often exhibit this condition, which may also be referred to as "baker's arms", "hot water bottle rash" or "toasted skin syndrome". Cho, et al., Effects of Infrared Radiation and Heat on Human Skin Aging in vivo, *The Society for Investigative Dermatology*, Vol. 14, pages 15-19, 2009, reports that IR-A can penetrate epidermal and dermal layers and reach subcutaneous tissues without noticeably increasing skin temperature. IR-B and IR-C are absorbed mostly in epidermal layers and cause increased skin temperature. Cho further states that repeated exposure to near IR has been shown to cause decreased type I procollagen expression and decreased expression of TGF-β1, β2 and β3 in human skin in vivo. Cho also reports that exposure to IR radiation can impact expression of MMP-1, cause degradation of extracellular proteins such as collagen and elastin fibers, decreased fibrillin production, elastosis, angiogenesis, and so on.

For at least these reasons it is desirable to create topical products that protect keratin surfaces such as skin or hair from IR radiation either alone or in conjunction with UV radiation protective effects.

Indium tin oxide ("ITO") is a ternary composition of indium, tin and oxygen in varying proportions. It is typically seen as a formulation of about 74% Indium, 18% oxygen, and 8% Sn by weight. Indium tin compositions can be present without oxygen, in which case they are referred to as "oxygen deficient ITO". ITO is used to coat industrial substrates such as windows, windshields, or other substrates where it is desired to reflect IR light. For example, it is used to assist in defrosting of aircraft windshields upon application of voltage. One advantage of ITO coated substrates is that they are transparent at wavelengths corresponding to visible light, and opaque in the IR and UV ranges. ITO is not known for use in consumer products, and particularly not in topical consumer products for protecting skin against IR radiation, or in compositions that are designed to protect skin from both UV and IR radiation.

It is an object of the invention to provide particles coated with ITO that have IR radiation protective effects when formulated into products for topical application to keratin surfaces. In one embodiment of the invention the particles coated with ITO are chemical or physical sunscreens in particulate form. In this case the particles exhibit both UV and IR protective effects. The ITO coated particles protect keratin surfaces from the adverse effects of IR radiation from all sources, but particularly solar IR radiation.

It is a further object of the invention to provide a topical composition for protecting keratin surfaces from the adverse effects of IR radiation containing ITO coated particles in an amount sufficient to protect against IR radiation.

It is a further object of the invention to provide a topical composition for protecting keratin surfaces from the adverse effects of UV and IR radiation containing chemical or physical sunscreen particles coated with ITO.

It is a further object of the invention to provide a method for protecting keratin surfaces from the adverse effects of IR radiation exposure by topically applying a composition containing ITO coated particles.

It is a further object of the invention to provide a method for protecting keratin surfaces from the adverse effects of UV and IR radiation by topically applying a composition containing ITO coated chemical or physical sunscreen particles.

BACKGROUND OF THE INVENTION

The invention is directed to a solid or hollow particle ranging from 0.001 to 200 microns in diameter coated with Indium Tin Oxide ("ITO"). The particle may be a pigment or powder. In one embodiment the particle may be a sunscreen such as zinc or titanium dioxide.

The invention is also directed to a topical composition containing a solid or hollow particle coated with ITO. The topical composition preferably blocks IR radiation, and in one preferred embodiment the particle coated with ITO is sunscreen particle and blocks both UV radiation due to the sunscreen particle with the ITO film coating blocking the IR radiation.

The invention is also directed to a topical UV protective composition containing a particle coated with ITO.

The invention is also directed to a method for protecting skin against solar IR radiation by topically applying a composition comprising at least one ITO coated particle.

The invention is also directed to a method for protecting skin from solar UV and IR radiation by topically applying a composition comprising at least one chemical or physical sunscreen in particulate form which is coated with ITO.

DETAILED DESCRIPTION

Definitions

All documents referred to herein are incorporated by reference in their entirety unless otherwise stated.

All percentages referred to herein are percentages by weight unless otherwise indicated.

The term "block" means, with respect to IR or UV radiation, that the radiation is blocked either in whole or in part from causing undesirable effects in the keratin surface either by physically blocking the radiation from reaching the surface, absorbing the radiation when it reaches the surface, or reflecting the radiation when it reaches the keratin surface.

The term "keratin surfaces" means skin, hair, or nails.

The term "topical" when used to refer to the composition means any composition that is applied to a keratin surface such as skin, hair, or nails.

Indium Tin Oxide

The ITO used in the invention may be oxygen deficient ITO, or a ternary mixture of indium, tin, and oxygen. The amount of each element may vary from 40-95% Indium, 5-35% oxygen, and 1 to 15% tin. One preferred form of ITO is a ternary mixture of 74% Indium, 18% oxygen, and 8% tin that may be identified by CAS No. 50926-11-9. ITO is most often in the form of a pale yellow to greenish powder depending on the concentration of $SnO_2$ present. The melting point ranges from 1500-1950° C. It is referred to as a transparent conducting oxide ("TCO") because of its electrical conductivity and optical transparency in the visible spectrum. Yet ITO is opaque in both the UV and IR wavelength ranges. ITO particles may be found in the nano range (7 to 75 nm) or standard fine grain powder particle sizes ranging from 0.1 to 15 microns, or agglomerated particles usually having a particle size greater than 30 microns, for example from 15 to 50 microns. The particles may be in the form of dispersions in water or organic solvents including mono- or dihydric alcohols such as ethanol, isopropanol, butylene glycol, propylene glycol, and the like. Examples include a dispersion of 30% ITO in isopropanol containing 90% Indium Oxide and 10% tin oxide or dispersions of 20% ITO in water. Other suitable forms include particles of various sizes such as nanoparticles (around 18 nm, or sizes less than 50 nm in diameter), particles of about 40-50 microns or more particularly having 43 microns, also referred to as −325 mesh. Other sources include Indium Corporation of America in Utica, N.Y. where ITO in particle sizes ranging from 0.01 to 50 microns is available.

Particles

In the preferred embodiment of the invention the ITO is coated onto particles used in cosmetics. Such particles may be pigments, powders, or combinations thereof. These particles may range from 0.001 to 200 microns in diameter. All, or a portion of the particles may be coated with ITO. The particles coated with ITO may include those set forth below:

A. Powders

The particles may be colored or non-colored (for example white) non-pigmented powders. Suitable non-pigmented powders include zinc oxide or titanium dioxide (which may be micronized, e.g. having a particle size of from about 0.01 to 1 micron and are generally known for having SPF properties, particularly UVA), bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be also be surface treated with lecithin, amino acids, mineral oil, silicone, or various other agents either alone or in combination, which coat the powder surface and render the particles more lipophilic in nature. Particularly preferred powders are silica such as that sold by Kiosi Corporation under the tradename Monoveil® which is a fine white powder having a particle size of 8 to 18 microns. This silica is in the form of a multi-lamellar silica membrane on the top of a skeletal internal silica structure. Another suitable silica is sold by Kobo Products under the trade name MSS-500W having an average particle size of 10 to 14 microns.

B. Pigments

The particles may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Composite particles may be suitable as well. Examples include spherical particles having a gaseous center sold under the trade name Expancel® 551, 820, 920, and DE having INCI names acrylonitrile/vinyl chloride/isobutene copolymer, acrylonitrile/vinylidene chloride/isobutene copolymer, acrylic acid/acrylonitrogens copolymer, isobutene/copolymer of acrylonitrile/methacrylate/acrylate copolymer, isobutene/copolymer of acrylonitrile/methacrylatelacrylate/water, and so on. If desired, these particles may be impregnated with other particles such as chemical or physical sunscreens according to the method set forth in Sojka, et al, U.S. Patent Application No. US2007/0071978.

Also suitable are particles referred to as Sunspheres® which are polymeric particles from styrene/acrylates copolymer sold by Dow Chemical Corporation. The styrene/acrylates copolymer particles have a particle size ranging from about 300 to 500 nanometers, more particularly about 400 nanometers. They may be coated with ingredients such as nonionic surfactants or glycols.

The Coating Method

The ITO may be coated on the particles in a variety of ways. It is preferred that the coating process be one that is operable at temperatures typically used in the preparation of cosmetic ingredients and formulations, which preferably range from room temperature to 350° C. In particular, in one embodiment the temperature at which the ITO coating is applied most desirably does not exceed 300° C.

One process for coating ITO onto the particles involves simply mixing ITO power with the particles to form mixtures of ITO and particles. This may be accomplished by physically combining the particles desired for treatment with the ITO. Ratios include from 5 to 80 parts particles to 80 to 5 parts ITO.

Another process for coating ITO onto the particles may accomplished by a process referred to as physical vapor deposition ("PVD") or sputter deposition which is a form of PVD. PVD uses physical forces to apply layers or coatings to the particulates. In PVD the desired particles may be prepared by drying them in an oven at sufficient temperature to remove any residual water. The drying may take place at temperatures ranging from 70 to 300° C., or at about 125° C. for a period of time to evaporate moisture. Depending on how much moisture is in the particles, this time can range from 1 to 24 hours. The dry particles are then put into a vacuum chamber and air is removed. A background pressure ranging from $10^{-6}$ to $10^{-4}$ torr may be used. A sputtering gas is then introduced. One example of a suitable gas may halogens such as argon or carbon tetrafluoride, and the like. The sputtering gas is added in an amount sufficient to obtain the desired background pressure in the system, which may range from 1 to 20 millitorr. The ITO is then introduced into the chamber. Alternatively, the indium and tin can be added and oxygen introduced into the chamber, however in this case the amount of oxygen present in the final product is not always consistent. In one embodiment the vacuum sputtering system may be operated in DC magnetron mode. The particles are tumbled slowly in the sputtering target with time and power chosen to produce coatings that are thick enough to provide particles that have the desired particle size. Sputtering times can range widely, from 2 to 25 hours with power levels also varying from 1 to 10 kilowatts. When the target is ITO it takes place in an oxygen free environment. After sputtering is concluded, if desired, the particles can be heated in air to dry. PVD is an effective and efficient coating process and provides a continuous, uniform, and strongly adherent coating of the ITO on the treated particles. PVD systems suitable for sputter coatings may be purchased from PVD Products, Wilmington, Mass. Examples of such systems include Magnetron Sputter Deposition Systems that may be in rectangular or cylindrical configurations and options for sputtering up or sputtering down. The chambers may be vacuum or cryogenic.

Also suitable as a coating method are chemical vapor deposition ("CVD") which is formation of a thin film on a substrate by chemical reaction of vapor phase precursors. The reaction occurs in the gas phase and on the substrate. CVD deposition of ITO films onto particles may be achieved by reacting indium metal acetate precursors such as indium acetate and tin acetate with the particles desired to be coated according to processes as disclosed in Maruyama and Tabata, Indium-Tin Oxide Thin Films Prepared by Chemical Vapor Deposition from Metal Acetates, Japanese Journal of Applied Physics, Volume 29, Part 2, No. 2 (1990).

It is also possible to coat particles using thermal methods, although in this case the particle to be coated must not be degraded upon exposure to the high temperatures required to deposit the coating. These temperatures may range from 300 to 1,000° C. In this application the ITO is heated with the particle in a high temperature furnace which causes the ITO to deposit on the surface of the particle. The temperature typically ranges from 1000 to 1200° C.

Various processes for depositing ITO onto particles may be found in Martin Friz and Friederich Waibel, *Coating Materials*, Springer Series in Optical Sciences, 2003, pages 105-130.

Pulsed laser deposition in high vacuum chamber which may be accompanied by reactive and ion-assisted sputtering is also a suitable deposition method.

Another suitable process is electrospinning sol-gel prepared ITO coatings on substrates followed by thermal processing as set forth in Zhang, et al., *Optical Materials* 26 (2004) pages 47-55. In this process sol-gel ITO is prepared and spin coating is used to apply the coating to the particles followed by heat treatment at temperatures ranging from 175 to 600° C.

Most preferred is where the ITO is coated onto particles using atomic layer deposition ("ALD"). Examples of ALD are set forth in Atomic Layer Deposition: An Overview, Chem. Rev. 2010, 110, pages 111-131 and Elam et al., Journal of Physical Chemistery, Vol 112, pages 1938-1945, 2008, U.S. Pat. No. 9,196,901; and U.S. Pat. No. 6,613,383 "Atomic Layer Controlled Deposition on Particle Surfaces", U.S. Pat. No. 6,713,177, "Insulating and Functionalizing Fine Metal Containing Particles with Conformal Ultra-thin Films; U.S. Pat. No. 6,913,827, "Nanocoated Primary Particles and Method for their Manufacture"; U.S. Pat. No. 7,132,697, "Nanomaterials for Quantum Tunneling Viarstors; U.S. Pat. No. 7,396,862, "Dental Composite Filler Particles"; U.S. Pat. No. 8,133,531, "Titanium Dioxide Particles Coated via an Atomic Layer Deposition Process; U.S. Pat. Nos. 8,163,336 and 8,637,156, "Methods for Producing Coated Phosphors and Host Material Particles Using Atomic Layer Deposition methods; and U.S. Pat. No. 8,187,731, "Metal Ferrite Spinel Energy Storage Devices and Methods for Making and Using Same, all of which are hereby incorporated by reference in their entirety. For example, ITO films can be applied by ALD using $In_2O_3$ and $SnO_2$ in a viscous flow reactor with nitrogen gas and at a set mass flow rate and a pressure of about 1 Torr. In particular, using alternating $InCp/O_3$ (cyclopentadienyl indium) exposures for $In_2O_3$ and TDMASn (tetrakis(dimethylamino)tin)/ $H_2O_2$ exposures for $SnO_2$ and adjusting the relative number of $In_2O_3$ and $SnO_2$ ALD cycles enables deposit of ITO films with more precision and control having a suitable thickness that can range from about 30-50 nanometers. A typical pattern of introducing reactants in an ALD reaction scheme involving two reagents takes place as follows: (1) introduce purge or fluidizing gas, (2) introduce the first reagent or a mixture of the first reagent and the carrier gas, (3) introduce the purge or fluidizing gas or pull a high vacuum to remove excess quantities of the first reagent as well as the reaction by-products, (4) introduce the second reagent or mixture of the carrier gas and the second reagent, (5) introduce the purge or fluidizing gas or pull a high vacuum to remove excess quantities of the second reagent and reaction by-products, (6) repeat steps 2-5 until the desired coating thickness is obtained. Suitable reaction temperatures may range from 250 to 1000K and pressure is typically subatmospheric. The preferred temperature is one at which the substrate is thermally stable. Preferred is where the coatings on the particles range from 10 to 100 Angstroms in thickness.

The ITO may be coated onto the particles with a suitable process that does not degrade the particles and is otherwise compatible with the ITO, the particle and the other ingredients used in the process. The coating may range in thickness from 0.1 to 1000 nanometers, or from 0.5 to 25% of the total particle by weight.

The Compositions

The ITO coated particles may be incorporated into a variety of compositions that may be in the anhydrous, emulsion, gel, or solution form. The ITO particles may range from 0.1 to 60%, preferably from about 0.5 to 50%, more preferably from about 1 to 40% by weight of the total composition.

The topical composition may contain other ingredients including but not limited to those set forth below:

A. Oils

In the event the compositions of the invention are in anhydrous or emulsion form, the composition will comprise an oil phase. Oily ingredients are desirable for the skin moisturizing and protective properties and may be present in amounts ranging from 0.1 to 80%. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

Suitable volatile oils generally have a viscosity ranging from about 0.5 to 5 centistokes 25° C. and include linear silicones, cyclic silicones, paraffinic hydrocarbons, or mixtures thereof. Examples include linear, cyclic, or branched volatile silicones available from commercial sources such as Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C. Branched volatile silicones include methyl trimethicone which may be purchased from Shin-Etsu Silicones under the tradename TMF-1.5, having a viscosity of 1.5 centistokes at 25° C.

Also suitable are volatile straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

A variety of nonvolatile oils are also suitable and may have a viscosity of greater than about 5 to 10 centistokes at 25° C., and may range in viscosity up to about 1,000,000 centipoise at 25° C. Examples of nonvolatile oils include, but are not limited to, esters, in the mono-, di-, or triester form including hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters".

Hydrocarbons are also suitable and include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Examples include dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

In the case where the compositions are in the form of aqueous solutions, dispersions or emulsions, in addition to water the aqueous phase may contain one or more aqueous phase structuring agents, that is, an agent that increases the viscosity or thickens, the aqueous phase of the composition. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides such as agar, agarose, *alicaligenes* polysaccharides, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

One type of suitable acrylate based polymeric thickener is sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

In the case where the composition is anhydrous or in the form of an emulsion, it may be desirable to include oil phase structuring agents. The term "oil phase structuring agent" means an ingredient or combination of ingredients, soluble or dispersible in the oil phase, which will increase the viscosity, or structure, the oil phase. The structuring agent itself may be present in the liquid, semi-solid, or solid form. Suggested ranges of structuring agent are from about 0.01 to 20%, preferably from about 0.05 to 15%, more preferably from about 0.1-10% by weight of the total composition. Suitable oil phase structuring agents include those that are silicone based or organic based.

Silicone based structuring agents include silicone elastomers, silicone gums, silicone waxes, linear silicones having a degree of polymerization that provides the silicone with a degree of viscosity such that when incorporated into the cosmetic composition it is capable of increasing the viscosity of the oil phase.

Silicone elastomers include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer, and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

Also suitable are silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

Silicone waxes are also suitable and include alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

Natural or synthetic waxes such as animal, vegetable, or mineral waxes may be used. Preferably such waxes will have a higher melting point such as from about 35 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, *citrus* wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

Synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like are suitable as well as silicas, silicates, silica silylate, and alkali metal or alkaline earth metal derivatives thereof. These silicas and silicates are generally found in the particulate form and include silica, silica silylate, magnesium aluminum silicate, and the like.

The composition may contain one or more organic surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, thermus thermophilis ferment extract, *Camelina sativa* seed oil, *Boswellia serrata* extract, olive extract, *Aribodopsis Thaliana* extract, *Acacia Dealbata* extract, *Acer Saccharinum* (sugar maple), acidopholus, acorus, aesculus, *Alicaligenes* polysaccharides, agaricus, agave, agrimonia, algae, aloe, *citrus*, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxrfraga sarmentosa, Vitis vinifera, Morus nigra, Scutellaria baicalensis, Anthemis nobilis, Salvia sclarea, Rosmarinus officianalis, Citrus medica limonum, Panax ginseng, Siegesbeckia orientalis, Fructus mume, Ascophyllum nodosum, Bifida* ferment lysate, *Glycine soja* extract, *Beta vulgaris, Haberlea rhodopensis, Polygonum cuspidatum, Citrus aurantium dulcis, Selaginella tamariscina, Humulus lupulus, Citrus reticulata* peel, *Punica granatum, Asparagopsis, Curcuma longa, Menyanthes trifoliata, Helianthus annuus, Hordeum vulgare, Cucumis sativus, Evernia prunastri, Evernia furfuracea*, and mixtures thereof.

It may also be desirable to include one or more sunscreens in the compositions of the invention. Such sunscreens include chemical UVA or UVB sunscreens or physical sunscreens in the particulate form.

The term "UVA sunscreen" means a chemical compound that blocks UV radiation in the wavelength range of about 320 to 400 nm. Preferred UVA sunscreens are dibenzoylmethane compounds including 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid.

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 10% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

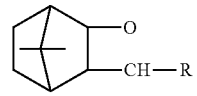

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

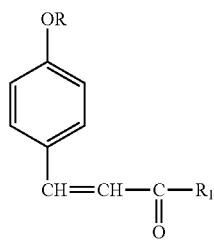

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

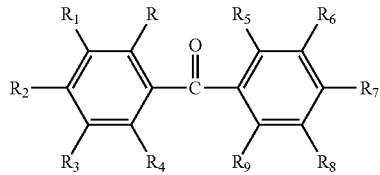

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

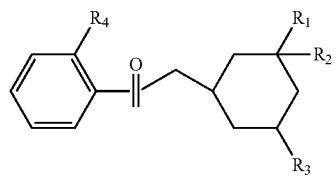

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and KR is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

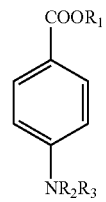

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

Also suitable are certain esters of 2-phenyl ethanol and benzoic acid. One example is phenyethyl benzoate, which is sold under the tradename X-Tend 226®, by International Specialty Products.

If desired, the compositions of the invention may be formulated to have a certain SPF (sun protective factor) values ranging from about 1-50, preferably about 2-45, most preferably about 5-30. Calculation of SPF values is well known in the art.

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, niacin, niacinamide, nicotinic acid, nicotinic acid dinucleotide, and so on, as well as coenzymes such as thiamine pyrophoshate, flavin adenine dinucleotide, folic acid, pyridoxal phosphate, tetrahydrofolic acid, and so on. Also Vitamin A and derivatives thereof are suitable. Examples are retinyl palmitate, retinol, retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

It may be desirable to include one or more film forming ingredients in the cosmetic compositions of the invention.

Suitable film formers are ingredients that contribute to formation of a film on the keratinous surface. If present, such film formers may range from about 0.01 to 50%, preferably from about 0.1 to 40%, more preferably from about 0.5 to 35% by weight of the total composition. Suitable silicone resins include trimethylsiloxysilicate, polymethylsilsesquioxane, dimethicone silylate, and mixtures thereof.

It may also be desirable to incorporate one or more DNA repair enzymes into the composition of the invention. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of a species of *micrococcus*), lecithin, and water. Photosomes® comprises a mixture of plankton extract (which is the extract of a biomass which includes enzymes from one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

The DNA repair enzymes may be present as components of botanical extracts, bacterial lysates, biological materials, and the like. For example, botanical extracts may contain DNA repair enzymes.

The compositions of the invention may be found in a variety of forms, such as anhydrous compositions, aqueous based solutions, serums, gels, skin creams or lotions, or color cosmetic compositions such as foundation makeup, mascara, lip color, blush, eyeshadow, and the like. Emulsions comprise from about 0.1 to 95%, preferably from about 1 to 90%, more preferably from about 2 to 85% water; and from about 0.1 to 95%, preferably from about 1 to 90%, more preferably from about 2 to 85% of one or more oils.

Suitable serums or gels will generally comprise from about 1-99% water, and optionally from about 0.001-30% of an aqueous phase thickening agent. The other ingredients mentioned herein may be present in the percentage ranges set forth. In the case where the cynaodiphenylacrylate is lipophilic it will be dispersed in the aqueous phase.

Typical skin creams or lotions comprise from about 5-98% water, 1-85% oil, and from about 0.1 to 20% of one or more surfactants. Preferably the surfactants are nonionic and may be in the form of oxyalkylenated organosiloxanes or organic nonionic surfactants.

Typical color cosmetic compositions such as foundations, blush, eyeshadow and the like will preferably contain from about 5-98% water, 1-85% oil, and from about 0.1 to 20% of one or more surfactants in addition to from about 0.1 to 65% of particulates that are pigments or a combination of pigments and powders.

Shampoos and conditioners contain large amounts of water, ranging from 10-95%, as well as surfactants from 0.01 to 20% and, if desired, oils or other conditioning ingredients.

Example 1

Sunscreen grade $TiO_2$ particles having a diameter ranging from 0.01 to 10 microns and ZnO particles of the same diameter may be coated with ITO by treating 500 mg of $TiO_2$ with ITO comprised of 90% InO and 10% SnO using a Magnetron Sputter Deposition System from PVD Products, Waltham, Mass. The $TiO_2$ particles are tumbled in a chamber while being sputter coated with the ITO using argon as the sputtering gas at a pressure of 3 millitorr and a power of 3 kilowatts, for about 150 minutes. No oxygen is added. The resulting particles are dried in an oven at 300° C. for 20 minutes.

Example 1A

Sunscreen grade $TiO_2$ particles having a diameter ranging from 0.01 to 10 microns and ZnO particles of the same diameter may be coated with ITO using ALD. About 500 mg of $TiO_2$ may be treated using a viscous flow reactor comprised of a circular stainless steel flow tube with an inside diameter of about 5 cm, which is suitable for holding particles. High purity nitrogen carrier gas is continuously passed through the flow tube at a mass flow rate of about 360 sccm and a pressure of 1 Torr. A constant reactor temperature is maintained by temperature controllers connected to resistive heaters. Four separate heating zones are used to ensure that temperature remains consistent along the length of the flow tube. ALD of $SnO_2$ is performed by using alternating exposures to TDMASn and $H_2O_2$. $In_2O_3$ ALD was performed using alternating exposures to InCp and ozone. The ozone is produced using a commercial ozone generator using a feed of high purity oxygen at a suitable flow rate. TDMASn and InCp were maintained in separate stainless teel containers at 40° C. and the tubing that connected the bubblers to the ALD reactor is heated to 150° C. to prevent condensation. High purity nitrogen gas is sent through the bubblers during the reaction and is diverted after the reaction. An ALD timing sequence is followed t1-t2-t3-t4 where t1 is the exposure time for the first precursor, t2 the second precursor, and so on with t4 being the purge time following exposure to the second precursor with units in seconds. Suitable timings are 24-2-2 for $In_2O_3$ and 1-5-1-5 for $SnO_2$. ITO ALD may be achieved by alternating cycles between InCp/O3 for In2O3 and TDMASn/H2O2 cycles for SnO2 ALD. The film composition is controlled by adjusting the % of $SnO_2$ cycles that are substituted for $In_2O_3$ cycles. Film deposition is measured using SEM.

Example 1B

The ALD procedure of Example 1 was used to coat silica particles (Monoveil® sold by Kiosi Corporation, Bohemia, N.Y.), 500 grams, with ITO. More specifically the particles were treated using ALD in a fluidized bed reactor as noted in Example 1 according to the procedure set forth in Journal of Physical Chemistry C., 2008, Vol. 112, pages 1938-1945. The particle sizes of the silica ranged from 8 to 18 microns in diameter. The thickness of the ITO coatings on the particles ranged from 0.5 to 15 nanometers, and specifically the thicknesses were 1, 3, and 10 nm.

Example 2

Red iron oxide, particle size about 15-30 microns are coated with ITO by treating 500 mg of red iron oxide with ITO comprised of 90% InO and 10% SnO. The iron oxide particles are tumbled in a chamber while being sputter coated with the ITO using argon as the sputtering gas at a pressure of 3 millitorr and a power of 3 kilowatts, for about 150 minutes. No oxygen is added. The resulting particles are dried in an oven at 300° C. for 20 minutes.

The particles prepared in Examples 1 and 2 may be tested for transmittance of IR radiation using a NIR spectrophotometer having a range of 190 to 2700 nm. Jasco, Inc., V-670 model.

Example 3

The particles of Example 1 are incorporated into a sunscreen composition as follows:

| Ingredient | Wt % | |
| --- | --- | --- |
| Water | QS | QS |
| Methyl trimethicone | 12.60 | 12.60 |
| Butylene glycol | 6.00 | 6.00 |
| Zinc oxide (treated as in Example 1) | 5.00 | 5.00 |
| Ethylhexylmethoxycrylene | 5.00 | 5.00 |
| C12-15 alkyl benzoate | 4.35 | 4.35 |
| ITO coated titanium dioxide (treated Example 1) | 3.88 | 3.1 |
| Dimethicone | 3.79 | 3.70 |
| Neopentylglycol diethylhexanoate | 3.46 | 3.46 |
| Beeswax | 3.00 | 3.00 |
| Dipentaerythrityl tripolyhydroxystearate | | 2.00 |
| Isododecane | 2.18 | |
| Glycerin | 2.00 | 2.00 |
| Lauryl PEG-9 polydimethylsiloxyethyl dimethicone | 2.00 | 2.00 |
| Ethyl macadamiate | 2.00 | 2.00 |
| Cetyl PEG/PPG 10/1 dimethicone | 1.00 | 1.00 |
| Dimethicone/dimethicone PEG/PPG 15 crosspolymer | 0.50 | 0.50 |
| Isostearic acid | 0.40 | 0.40 |
| Trisiloxane | | 0.36 |
| Trimethylsiloxysilicate | 0.33 | 0.33 |
| Acrylates copolymer | | 0.30 |
| Polyhydroxystearic acid | 0.25 | 0.25 |
| Xanthan gum | 0.25 | 0.25 |
| Dimethicone silylate | | 0.24 |
| Disteardimonium hectorite | 0.24 | |
| Dimethicone/vinyl dimethicone crosspolymer | 0.15 | 0.15 |
| Lecithin | 0.01 | 0.01 |

The compositions were prepared by combining the ingredients well and mixing to form an emulsion.

Example 4

An anhydrous product with SPF is prepared as follows:

| Ingredients | w/w % |
| --- | --- |
| Ethylhexyl methoxycinnamate | 7.50 |
| Polyethylene | 6.00 |
| Heptyl undecylenate | 6.00 |
| Ethylhexylmethoxycrylene | 6.00 |
| Bis-diglyeryl polyacyladipate-2 | 5.29 |
| Homosalate | 5.00 |
| Mica/Aluminum Dimyristate/triethoxcaprylylsilane/disodium stearoyl glutamate | 5.00 |
| ITO coated mica/methylmethacrylate crosspolymer | 5.00 |
| Ethylhexyl salicylate | 5.00 |
| Microcrystalline wax | 4.50 |
| *Simmondsia Chinensis* (jojoba) seed oil | 4.00 |
| Butyloctyl salicylate | 4.00 |
| Glyceryl hydrogenated rosinate | 4.00 |
| Oleic/linoleic/linolenic polyglyceride | 4.00 |
| HDI/trimethylol hexyllactone crosspolymer/silica | 3.50 |
| Avobenzone | 3.00 |
| Polyglyceryl-2 triisostearate | 2.81 |
| Octocrylene | 2.79 |
| Synthetic wax/synthetic beeswax/stearic acid | 2.40 |
| Ethyl macadamiate | 2.00 |
| *Butyrospermum parkii* (Shea Butter) | 2.00 |
| Beeswax | 1.80 |
| Methyl glucose sesquistearate | 1.50 |
| Dipentaerythrityl hexahydroxystearate/hexastearate/hexarosinate | 1.49 |
| Glyceryl dilaurate | 1.00 |
| VP/Eicosene | 1.00 |
| Isononyl isononanoate | QS |

Example 5

Skin treatment oil-in-water (1), and oil-in-water-in-silicone oil (2), creams may be prepared as follows:

| | w/w % | |
| --- | --- | --- |
| Ingredient | 1 | 2 |
| Water | QS | QS |
| Hydroxyethyl urea | 0.50 | |
| Hyaluronic acid | 9.00 | 9.00 |
| Creatine | 0.05 | |
| Sucrose | 0.50 | |
| Caffeine | 0.20 | |
| Caprylyl glycol | 0.40 | 0.28 |
| Caprylic/capric triglyceride/cetyl alcohol/C12-20 acid PEG-8 ester | 4.00 | |
| PEG-100 stearate | 1.20 | |
| C12-20 acid PEG-8 ester | 4.96 | |
| Caprylic/capric triglyceride | 0.55 | |
| Behenyl alcohol | 0.50 | |
| Coco caprylate caprate | 5.10 | |
| Sweet almond oil | 0.10 | |
| Dimethicone, 100 cst. | 2.50 | |
| Ethylhexylmethoxycrylene | 2.00 | 2.00 |
| Dimethicone, 6 cst | | 5.00 |
| Dimethicone (silicone gum/20 cst dimethicone blend) | | 8.00 |
| Dimethicone/polysilicone 11 | | 6.00 |
| Dimethicone/dimethicone PEG-10/15 crosspolymer | | 1.00 |
| Lauryl PEG-9 polydimethylsiloxyethyl dimethicone | | 1.00 |
| Wheat bran extract/olive extract | 0.20 | 0.20 |
| Cholesterol | 0.20 | |
| Linoleic acid | 0.20 | |
| Cholesterol/potassium sulfate | 0.20 | |
| *Theobroma grandiflorum* seed butter | 1.40 | |
| Lauryl PCA | 0.01 | 1.00 |
| Dimethicone | 1.50 | |
| Glycerin | 2.00 | |
| Butylene glycol | 1.00 | |

-continued

| Ingredient | w/w % | |
|---|---|---|
| | 1 | 2 |
| Hexylene glycol | | 0.05 |
| ITO coated mica/titanium dioxide | 1.00 | 0.75 |
| ITO coated mica/titanium dioxide/triethoxycaprylyl silane | | 0.50 |
| Pearl powder | 0.001 | |
| Silica | 0.50 | |
| N-acetyl glucosamine | 1.00 | 1.00 |
| Water/purified *Aribodopsis Thaliana* extract/lecithin | 0.50 | 1.00 |
| Aqueous solution acetyl hexapeptide-8 | 1.00 | 1.00 |
| Yeast ferment extract | 1.00 | 1.00 |
| Water/lecithin/micrococcus lysate | 0.50 | 0.50 |
| Butylene glycol | 0.50 | |
| *Boswellia Serrata* extract | 0.05 | |
| *Calophyllum Inophyllum* (tamanu) seed oil | 0.05 | |
| Sodium acrylate/sodium acryloyldimethyl taurate copolymer/hydrogenated polydecene/laureth-8 | 1.00 | 1.00 |
| Ammonium acrylodimethyltaurate/VP copolymer | | 0.70 |

The composition is prepared by combining the water phase and oil phase ingredients separately, then emulsifying to form an emulsion.

Example 6

Emulsion foundation makeup compositions are prepared as follows:

| Ingredient | w/w % |
|---|---|
| Cyclomethicone | 16.90 |
| Polysilicone-11 | 5.00 |
| Cyclomethicone/dimethiconol | 1.00 |
| Dimethicone copolyol | 1.50 |
| Sorbitan sesquioleate | 1.50 |
| Phenyl trimethicone | 10.00 |
| Dimethicone | 10.00 |
| ITO treated red Iron Oxide treated with methicone | 0.50 |
| ITO treated yellow iron oxide treated with methicone | 1.22 |
| ITO treated black iron oxide treated with methicone | 0.13 |
| ITO treated titanium dioxide coated with methicone | 8.06 |
| Water | QS |
| Butylene glycol | 5.00 |
| Xanthan gum | 0.10 |

-continued

| Ingredient | w/w % |
|---|---|
| Magnesium sulfate | 1.00 |
| Laureth-7 | 0.25 |

The water, oil and pigment phases are separately prepared by low shear mixing. The phases are combined with high shear blending to form a foundation makeup composition.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A topical emulsion composition comprising a solid or hollow particle ranging from 0.001 to 200 microns in diameter coated with Indium Tin Oxide ("ITO").

2. The composition of claim 1 which is in the form of a water and oil emulsion.

3. The composition of claim 1 additionally containing one or more chemical sunscreens.

4. The composition of claim 2 the form of a water and oil emulsion skin cream or lotion comprising 5 to 98% water, 1 to 85% oil and from 0.1 to 20% surfactants.

5. The composition of claim 4 wherein the surfactants are oxyalkylenated organosiloxanes or organic nonionic surfactants.

6. The composition of claim 1 which is in the form of a foundation, blush, or eyeshadow additionally comprising 0.1 to 65% of particulates in the form of pigments or a mixture of pigments and powders.

7. The composition of claim 1 further comprising a UVA or UVB sunscreen.

8. The composition of claim 1 which is a shampoo or conditioner.

9. A topical composition in the form of a serum or gel comprising 1-99% water and 0.0001 to 30% of an aqueous based thickening agent and further comprising a solid or hollow particle ranging from 0.001 to 200 microns in diameter coated with Indium Tin Oxide ("ITO").

* * * * *